United States Patent [19]

Logé

[11] Patent Number: 5,653,591

[45] Date of Patent: Aug. 5, 1997

[54] DENTAL TOOTH CLEANING INSTRUMENT WITH A MECHANICALLY DRIVEN TOOTH CLEANING TOOL

[75] Inventor: Hans Logé, Biberach, Germany

[73] Assignee: Kaltenbach & Voigt GmbH & Co., Biberach an der Riss, Germany

[21] Appl. No.: 671,080

[22] Filed: Jun. 27, 1996

Related U.S. Application Data

[63] Continuation of Ser. No. 268,648, Jun. 30, 1994, abandoned.

[30] Foreign Application Priority Data

Aug. 2, 1993 [DE] Germany .................. 43 25 933.2

[51] Int. Cl.⁶ .................................................. A61C 3/03
[52] U.S. Cl. .................. 433/118; 433/124; 433/126; 433/82
[58] Field of Search ...................... 433/82, 118, 119, 433/120, 126, 124

[56] References Cited

U.S. PATENT DOCUMENTS

| | | |
|---|---|---|
| 3,978,852 | 9/1976 | Annoni ................................. 433/118 |
| 4,578,033 | 3/1986 | Mössle et al. ........................ 433/29 |
| 4,589,847 | 5/1986 | Logé et al. ........................... 433/126 |
| 4,787,847 | 11/1988 | Martin et al. ........................ 433/119 |
| 4,880,382 | 11/1989 | Moret et al. ......................... 433/118 |
| 4,991,249 | 2/1991 | Suroff ................................... 433/119 |
| 5,000,684 | 3/1991 | Odrich ................................. 433/118 |
| 5,071,348 | 12/1991 | Woog ................................... 433/118 |
| 5,308,242 | 5/1994 | McLaughlin et al. .............. 433/126 |

FOREIGN PATENT DOCUMENTS 245628  11/1987  European Pat. Off. ............. 433/82

*Primary Examiner*—Ren Yan
*Attorney, Agent, or Firm*—Scully, Scott, Murphy & Presser

[57] ABSTRACT

In a tooth cleaning instrument (1) with an elongate handpiece, which carries a tooth cleaning tool (3) on its forward end, which can be set into vibration by a motor driven vibration generator (7) which is associated with the tooth cleaning instrument (1), whereby the tooth cleaning instrument (1) is connected or is detachably connectable at its rear end to a supply hose (6) having energy and/or media supply lines, the tooth contact element (17) is areal or quasi-areal and has a surface structure which is suitable for the abrasion of the tooth coating.

15 Claims, 2 Drawing Sheets

DENTAL TOOTH CLEANING INSTRUMENT WITH A MECHANICALLY DRIVEN TOOTH CLEANING TOOL

This is a continuation of application Ser. No. 08/268,648 filed on Jun. 30, 1994 abandoned.

BACKGROUND OF THE INVENTION

1. Field of the Invention

In the field of dental hygiene there exist a plurality of tooth cleaning instruments. Of these firstly the mechanical toothbrush intended for everyday use must be mentioned, which serves not only for cleaning the teeth of food remnants but also serves for cleaning of the tooth spaces and of the gums, thereby serving as means for cleaning the oral cavity, and is operated by the person owning the oral cavity. With this tooth cleaning instrument, lightly adhering coatings or films as well as the food remnants are removed from the teeth, whereby this tooth cleaning instrument serves also to clean the spaces between the teeth and the transitions between the necks of the teeth and the gums. Such a tooth cleaning instrument is a brush with a plurality of relatively soft bristles, of which usually a plurality of bristle groups arranged with small spacings between one another are provided. The mechanical driving of such a toothbrush takes place with a higher frequency and with a smaller amplitude than is the case with manually operated toothbrushes. As action upon the gums with excessive pressure is harmful, mechanically driven toothbrushes having a pressure sensor which generates a visible warning signal, when a loading of the toothbrush directed transversely of the bristle shaft exceeds a predetermined value, have been developed.

2. Discussion of the Prior Art

On the other hand there exist tooth cleaning instruments, namely so-called tartar removal devices, which are utilized by the dentist in his practice for the treatment of patients. These are mechanically-driven tartar removal devices with a wire-form tool with only one tip, which is mechanically driven at a high frequency and a small amplitude whereby the hard metal tip of the instrument, which is curved in the manner of a beak, is driven by vibrations which are directed transversely of its shaft and therefore—because of the arced beak form of the curved tip—impacts the surface of the teeth, gently however, and is capable of removing even firmly adhering tartar.

There are also very thin films on teeth, such as tooth surface discolorations, for which an above-described tartar removal device is not suitable.

For cleaning the teeth of surface discolorations an apparatus has become known in which a cleaning powder mixed with warm water is squirted onto the tooth surface under pressure, whereby the surface discolorations are removed by the cleaning powder. A water-soluble cleaning powder such as sodium carbonate is utilized, which dissolves in water during treatment, so that no granular remains are left in the oral cavity. The water is removed from the mouth by means of a suction apparatus. Although this tooth cleaning instrument, which is likewise for use by a dentist, has proved itself in practice, the treatment is unpleasant, in particular for sensitive patients, as its leaves an unusual taste in the mouth on account of the sodium carbonate. Also, this known tooth cleaning instrument may not be used for such patients who must to keep to a low-salt diet, who suffer from a severe illness affecting the respiratory organs and wear contact lenses.

SUMMARY OF THE INVENTION

The object of the invention is to form a dental tooth cleaning instrument of the kind mentioned in the introduction in such a way that it is capable of removing tooth coatings as well as discolorations on the tooth surface.

The tooth cleaning instrument according to the invention is effective with its tooth contact element not only punctually but arealy. Hereby it is not only more efficient, but is capable also of cleaning or removing discolorations of the tooth surface rapidly and efficiently. The tartar removal device generally used in this field is also quite efficient in removing coatings on teeth, such as tartar, because the tartar breaks away during the treatment, but with this tartar removal device the remaining traces of tartar can be cleaned or removed only with great operational and time consuming efforts. In contrast the tooth cleaning apparatus according to the present invention makes possible an efficient cleaning or an efficient removal also of tartar remains. It is also advantageous and rational to utilize the tooth cleaning instrument according to the invention for the cleaning or removal of discolorations of the tooth surface. On account of the areal working, remaining areas of discoloration can also be removed with little operational and time consuming effort.

Within the scope of the invention it is possible to drive the tooth cleaning instrument according to the invention with vibrations so that it is effective parallel to and/or transversely of the tooth surface, i.e. rubbing and/or impacting the tooth surface. Thereby the areal working of the tooth cleaning tool according to the invention makes possible the above-mentioned rational operation on the one hand and on the other hand a simultaneous and uniform cleaning of a relatively large surface part of the tooth surface, which is important in particular for the removal of discoloration, in order to achieve an even natural colour of the treated surface.

The invention is directed to features which contribute to problem solving, improve the efficacy of the tooth cleaning instrument, make possible different cleaning measures through an exchange of different tooth cleaning tools, ensure an advantageous illumination and/or cooling and/or rinsing of the surface under treatment and further result in simple, practical economically manufacturable constructions.

BRIEF DESCRIPTIONS OF THE DRAWINGS

In the following the invention and further advantages thereby achievable will be explained in more detail with reference to preferred embodiments. There are shown:

FIG. 1 a tooth cleaning instrument according to the invention, in a side view;

FIG. 2 the forward end of the tooth cleaning instrument with a tooth cleaning tool in an enlarged illustration and partly in axial section;

FIG. 3 a protection cover for the head of the tooth cleaning tool, in axial section;

FIG. 4 a cleaning head for the tooth cleaning tool in axial section and in a modified configuration.

DETAILED DESCRIPTION OF PREFERRED EMBODIMENTS

Figure 1:
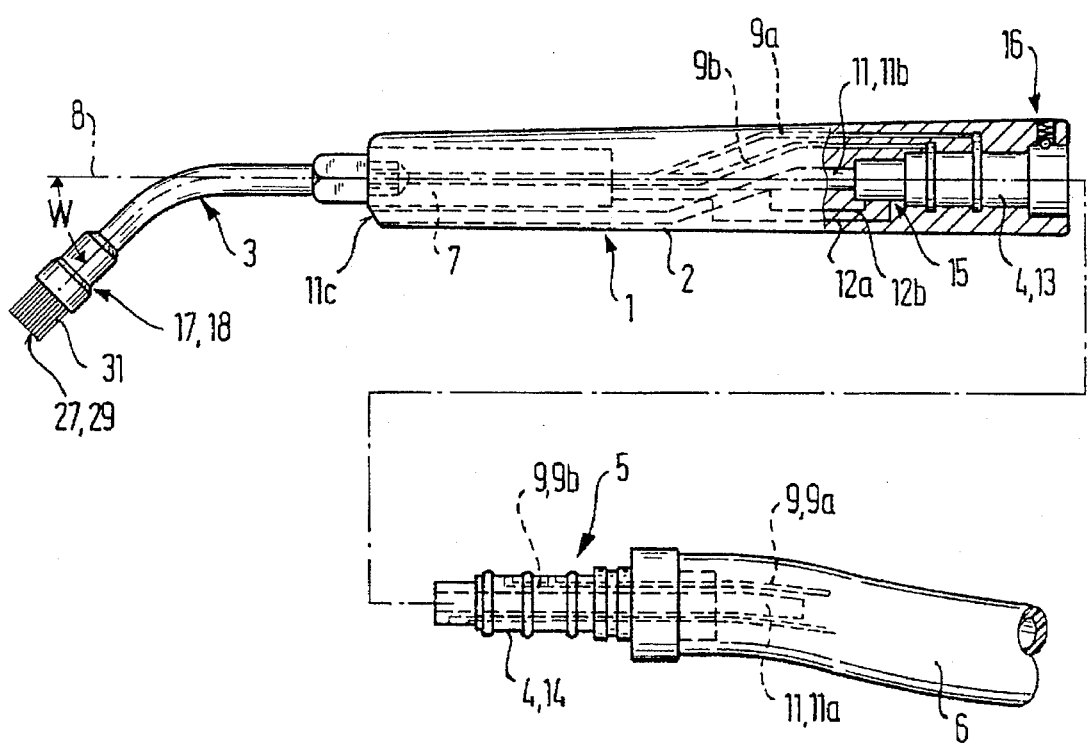
Figure 2:
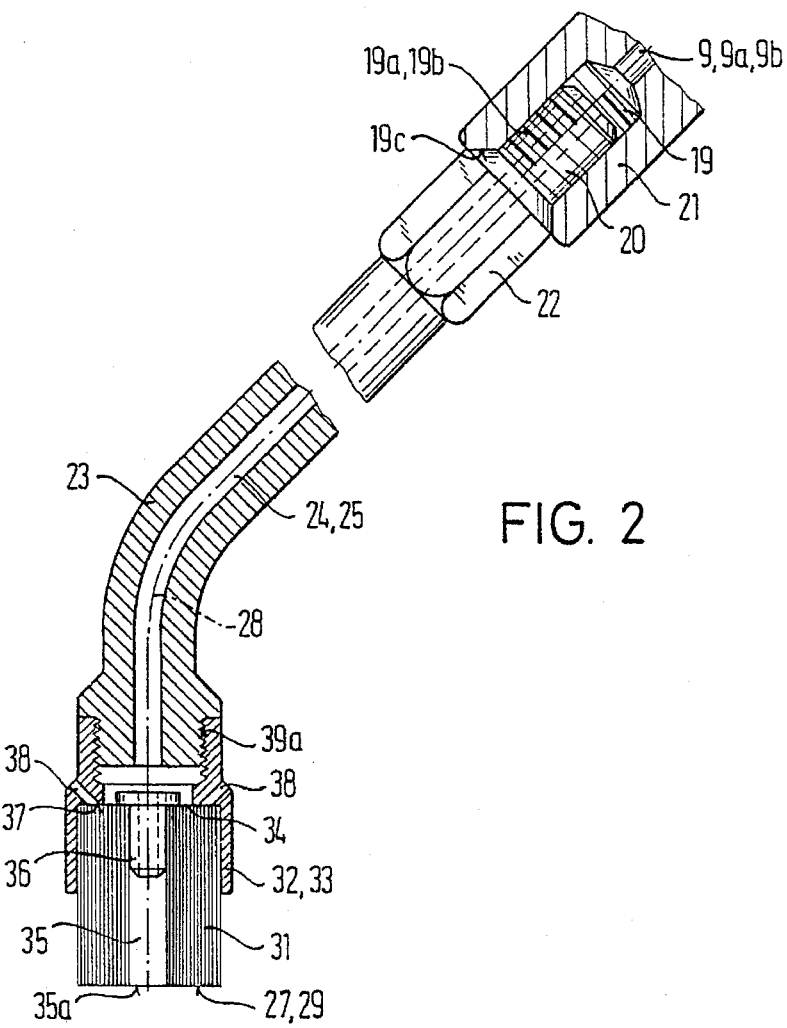

The main parts of the tooth cleaning instrument 1 in the form of a handpiece are a grip sleeve 2, which carries detachably at its forward end a tooth cleaning tool 3 and is detachably connected at its rear end with a connecting piece 5 by means of a quick coupling or a so-called plug-in/rotating coupling 4, which coupling piece is attached to the forward end of a flexible supply hose 6.

In the forward region of the grip sleeve 2 a schematically indicated vibration generator 7 is arranged which is mounted in the grip sleeve and connected with the tooth cleaning tool 3 in such a way that it is capable of transmitting vibrations directed longitudinally or transversely of the centre axis 8 of the grip sleeve 2 to the tooth cleaning tool 3 which projects forwardly from the grip sleeve 2.

Several supply lines run through the supply hose 6, the plug-in/rotating coupling 4 and the grip sleeve 2, whereby in the present embodiment these are a supply line 9 for compressed air and/or rinsing fluid, in particular water, whereby a spray can also be used, a supply line 11, which serves for illuminating the treatment area, and two supply lines 12a, 12b, which are electric supply lines of an electric circuit to which the electric vibration generator 7 is connected.

The plug-in/rotating coupling 4 is formed with a coupling recess 13 which is round in section and a coupling pin 14, which can be plugged into and can rotate in the recess, whereby the coupling pin 14 may be arranged directed rearwardly from the grip sleeve 2 and the coupling recess may be arranged in the forward end of the connecting piece 5 or—as in the present embodiment—the coupling recess 13 can be arranged on the rearward end of grip sleeve 2 and the coupling pin 14 can be arranged forwardly projecting from the connecting piece 5.

The supply lines are separable and reconnectable in the region of the plug-in/rotating coupling 4, so that upon detachment and mounting of the grip sleeve 2 from and onto the connecting piece 5 the supply line sections are separated and reconnected with one another self-actingly. Here, configurations which are known per se may be employed.

With the present embodiment the supply line 11 penetrates the plug-in/rotating coupling 4 coaxially and is formed with a light conductor, known per se, made of glass or plastics and/or glass or plastics fibres, the light conductor sections 11a, 11b of which light conductor are separated at the forward end of the coupling pin 14 and lie oppositely facing one another in the coupled condition.

For the supply of cooling or rinsing fluid, or a spray and compressed air, there are provided one common or two supply lines 9a, 9b, which first run axially in the coupling pin 14, radially cross the separating line of the plug-in/rotating coupling in a sealed manner and are then again axially continued in the grip sleeve 2, whereby at the separating line a circumferential groove is arranged in the coupling pin 14 or in the wall of the coupling recess 13. Hereby an unrestricted rotation of the grip sleeve 2 is possible without interruption of the passage of the media.

A corresponding path with radial crossing of the separating line of the plug-in/rotating coupling 4 is also provided for the electric supply lines 12a, 12b, whereby sliding rings and contacts cooperating therewith are arranged at the separating line at 15, so that the current supply and discharge is also independent of a rotation of the grip sleeve 2.

A catch device 16, engaging and disengaging self-actingly, is also associated with the plug-in/rotating coupling 4, whereby an unintended de-coupling is prevented. Such a catch device 16, known per se, can be provided by a radially spring mounted catch element, e.g. a ball, preferably in the grip sleeve 2, which cooperates with a circumferential groove, preferably on the coupling pin 14.

A plug-in/rotating coupling 4 as described above, together with the supply lines which penetrate it, is described in several embodiments in U.S. Pat. Nos. 4,578,033 and 4,589, 847, both of which are commonly assigned to the assignee of the present application. Therefore, for rational reasons, this plug-in/rotating coupling 4 will not be further described in specific detail, but reference is made to the fullest extent of embodiments described in the above-mentioned publications.

The tooth cleaning tool 3 is a rod-shaped component, obtusely angled at its free end, namely the tooth contact element or tool head 17, connected preferably detachably with the grip sleeve 2 at its rearward end, and carries—preferably detachably—a cleaning head 18 at its forward end. For the attachment of the tooth cleaning tool 3 a screw connection can be provided preferably having an external thread 19a on a rearward threaded pin of the tooth cleaning tool 3 and an internal thread 19b in a corresponding in particular coaxial threaded hole of the grip sleeve 2 or of a base part 21 which supports the vibration generator and is vibratably mounted inside the grip sleeve 2. In the rearward end region of the tooth cleaning tool 3 there is arranged an element by means of which rotation can be effected, preferably having the form of a square or hexagonal 22 for a spanner, with which the tooth cleaning tool 3 can be either mounted or dismounted. The shaft 23 of the tooth cleaning tool 3 is preferably formed by a pipe having a comparatively thick wall, the free space of which can serve as a supply line for compressed air and/or rinsing fluid or a spray. In the present configuration the common supply line 9 for compressed air and/or rinsing fluid or spray opens into the cavity 24 of shaft 23 in the form of a channel or pipeline in the grip sleeve 2a, whereby the associated channel 25 opens coaxially forwardly into the threaded hole 19. The tight sealing of the screw connection is ensured by a seal on the free edge of the threaded hole 19, in this case an interior cone surface 19c on the edge of the threaded hole 19 and a correspondingly formed exterior cone surface in the foot region of the threaded pin 20.

The cleaning head 18 has a plurality of cleaning tips 27, which lie with small spacings from one another in a working surface 29 arranged transversely of the longitudinal middle axis 28 of the head, which surface may be either flat, curved or, as in the present embodiment, flat and radial.

In the present embodiment the cleaning head 18 has a plurality of thin pins or wires 31 which are arranged axis parallel and may have small spacings from one another or preferably lie against one another, thereby being able to form a wire bundle. The individual wires 31 consist of a material which is capable of removing a tooth coating and preferably also a discoloration of the tooth surface through the vibration movement into which the tool is set during operation. The wires 31 are therefore of a material which is preferably harder than the tooth surface and for this purpose metal wires and preferably spring steel wires in particular of stainless steel, are suitable. The cross sectional size of the wires 31 is approximately 0.02 mm to 0.2 mm, preferably approximately 0.05 mm to 0.08 mm.

The wires 31 are bundled and are undetachably connected to a socket 32 which is detachably connected with the shaft 23 by means of a securable plug-in socket or by a screw connection. The socket 32 preferably has a sleeve 33, into which the wire packet is received in the manner of a pot and is therein attached e.g. by means of a clamping effect, gluing, welding, in particular laser welding, or soldering, preferably hard soldering.

As a prefabricatable component, the wire packet can be either glued, welded or soldered, in particular hard-soldered or laser-welded, to its mounting at its rear side 34. The mounting in the socket 32 can be formed by the same gluing, welding or soldering or by means of a special gluing, welding or soldering or even by squashing the circumferential wall of the sleeve 33.

Preferably the wires 31 are arranged in a ring form so that they enclose a longitudinal channel 35 which is an extension of the hollow space 24 and thereby forms a supply line section for compressed air and/or rinsing fluid or spray. Thereby these media strike in a position which is favourable with regard to the treatment area, namely at or in the working surface 29. To facilitate the manufacturing or to improve the stability of the wire packet an interior sleeve 36 can be arranged in the rearward region of the longitudinal channel 35, if appropriate with a flange engaging behind the rear side 34, and can preferably be fixed in the channel by gluing, welding or soldering. Preferably the sleeve 33 has an internal shoulder 37, which can serve for rearward support of the wire packet. In the region of this internal shoulder 37 one or several transverse bores 38 may be arranged in the sleeve 33, distributed around the circumference, which can serve for the gluing, welding or soldering.

With the present screw connection for the cleaning head 18 or the socket 32, the sleeve 33 which is preferably tapered towards the rear in the region of the internal shoulder 37 or the transverse bores 38 has an internal thread 39a with which it is screwed onto an external thread on the forward end of the shaft 23, which is preferably possible by virtue of a not illustrated element by means of which rotation can be effected, to which a turning tool can be applied.

With the present embodiment the wire packet is round in section, whereby its external diameter is approximately 3 mm and the diameter of the longitudinal channel 35 is approximately 1 mm. The length L of the wires 31 is approximately 3 mm to 10 mm, preferably approximately 6 mm.

Figure 3:
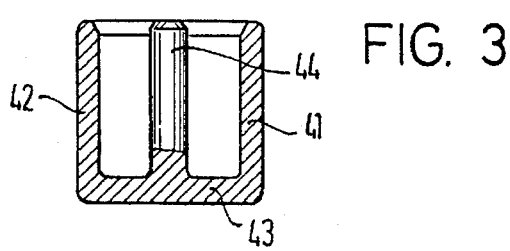

As the wire tips are sensitive elements, it is advantageous to provide the cleaning head 18 with a protection cap 41, which effectively protects the wires when not in use. The protection cap illustrated in FIG. 3 consists of a cylindrical circumferential wall 42, a cover wall 43 and a pin 44, which can be plugged into the longitudinal channel 35 with little play for movement. Preferably the outside edge of sleeve 33 and/or the inner edge of the circumferential wall 42 and/or the tip of the pin 44 are rounded or chamfered to facilitate the slipping on of the protection cap 41. In the mounted position the circumferential wall 42 or the pin 44 can cooperate with the wires 31 in a radially clamping manner. It is also advantageous to make the circumferential wall 42 so large that it overlaps the sleeve 33, whereby it can cooperate with the sleeve in a clamping manner. If the pin 44 is of such a length that the free end thereof lies against the interior sleeve 36 and a spacing remains between the cover wall 43 and the wire tips, the wire tips are spared from contact with the cover plate 43 and are protected against damage.

Figure 4:
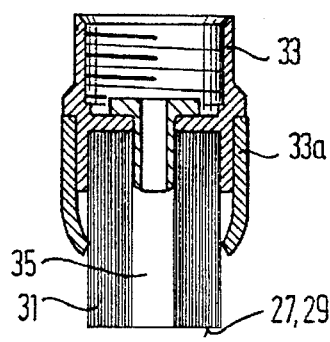

With the embodiment according to FIG. 4, in which similar or comparable parts are designated with the same reference signs, the wire packet is received in a sleeve 33, which preferably is externally tapered relative to the rearward end of the sleeve 33, whereby a cover sleeve 33a sits on the sleeve 33, which cover sleeve is preferably pushed on after fastening of the wire packet in the sleeve 33, whereby simple manufacture and a neat finish are achieved. The forward edge region of the cover sleeve 33a may be rolled inwards, whereby it may restrict or radially clamp in the wire packet.

Preferably there are several different cleaning heads 18 associated with the tooth cleaning tool 1, which heads are freely interchangeable. These may be of differing sizes, forms and frictional properties or even hardness.

Within the scope of the invention, instead of utilizing the above-described brush cleaning head 18, it is possible to utilize a cleaning head of, if appropriate, profiled rubber or plastics with embedded abrasive or with an abrasive at the working surface 29.

The cleaning body described in all the above-mentioned embodiments can be made of hard material or hard elastic material, the working surface 29 of which is either stable in shape, or of a soft elastic material, the working surface 29 of which is so soft elastic in itself that it can follow the contour of the tooth surface or spaces between the teeth, thereby adapting its shape thereto, when the person carrying out the treatment exerts pressure.

The abrasive efficacy of the cleaning tips 27 or wire tips can be improved by a coating with hard substances, in particular of metal.

In order to switch on the tooth cleaning tool 1 and/or the vibration generator 7 and/or one of the media (compressed air, rinsing fluid, in particular water, or spray, light), one or several switches in the form of hand switches (not shown) can be provided on the tooth cleaning tool 1 or on the grip sleeve 2, or a correspondingly formed foot switch can be provided.

The light conductor section 11b ends in a light exit opening 11c at the forward end of grip sleeve 2, in particular on the side towards which the tool head 17 is angled. The light exit opening 46 is directed towards the treatment location or the tooth cleaning head 17.

On account of the angled arrangement of the cleaning head 18 with regard to the longitudinal middle axis of the preferably straight grip sleeve 2 there results a position of the cleaning head 18 from which it is easy to operate with regard to the expected tooth dispositions, whereby also poorly accessible tooth surfaces can be readily reached. The angle W at which the cleaning head 18 is angled, is approximately 20 to 50 degrees, preferably 30 to 45 degrees.

Tests have shown that in particular with a working surface 29 which is formed with cleaning tips 27 or wires 31 or bristles an efficient cleaning of the tooth surface is achieved when the cleaning tips act on the surface abrasively and/or with gentle impacting. This mode of operation is achieved preferably by means of an angled cleaning head 18.

I claim:

1. Dental tooth cleaning instrument including an elongate handpiece comprising a gripping sleeve; a tooth cleaning tool having a cleaning head on a shaft mounting said tool; a motor-driven vibration generator being arranged in the gripping sleeve, said generator comprising a base part vibratably mounted in a forward end portion of the gripping sleeve, a rear end of the gripping sleeve being detachably connectable with a connecting piece by a rotatable plug-in coupling formed with a coupling pin and a coupling recess for receiving said pin; a rear end of the shaft being detachably connected with the base part; an element arranged at the forward end portion of the shaft through which rotation is effected for alternatively tightening and releasing a screw connection; the cleaning head being detachably connected to the forward end of the shaft by said screw connection; the cleaning head having a plurality of wires at a forward end thereof, said wires lying laterally side by side and ending in a common working surface and being attached in a pot-shaped sleeve of the cleaning head, said sleeve receiving and enclosing the wires; a selective rinsing and cooling device which includes a medium channel extending longitudinally from the coupling piece through the gripping sleeve, the base part, the shaft, the wire packet and ends at the working surface thereof, the shaft being angled within a range of about 20° to 50° relative to the cleaning head; an illumination device in the gripping sleeve, said illumination device having a light-exiting opening at the forward end of the gripping sleeve on the side towards which the shaft is angled; and including a plurality of different and selectively interchangeable cleaning heads.

2. Tooth cleaning instrument according to claim 1, wherein said plurality of wires comprise tooth cleaning tips which lie in defining surface plane which extends transversely of a longitudinal central axis of said cleaning head.

3. Tooth cleaning instrument according to claim 1, wherein the plurality of wires extends in a longitudinal direction and arranged radially in side-by-side relationship.

4. Tooth cleaning instrument according to claim 3, wherein the wires are constituted of an elastic, corrosion-resistant material.

5. Tooth cleaning instrument according to claim 4, wherein said material comprises a metal.

6. Tooth cleaning instrument according to claim 5, wherein said metal comprises a stainless spring steel.

7. Tooth cleaning instrument according to claim 4, wherein said material comprises a hard plastic.

8. Tooth cleaning instrument according to claim 4, wherein the wires each have a cross-sectional dimension of approximately 0.02 to 0.2 mm.

9. Tooth cleaning instrument according to claim 4, wherein the wires each have a cross-sectional dimension of approximately 0.05 to 0.08 mm.

10. Tooth cleaning instrument according to claim 4, wherein the wires lie against one another.

11. Tooth cleaning instrument according to claim 1, wherein the wires are formed by frictionally abrasive grains which are applied onto or embedded in the pot-shaped sleeve.

12. Tooth cleaning instrument according to claim 11, wherein the pot-shaped sleeve consists of a material which is stable in shape or elastically deformable.

13. Tooth cleaning instrument according to claim 11, wherein the pot-shaped sleeve is tubular shaft.

14. Tooth cleaning instrument according to claim 1, wherein said plurality of cleaning heads are provided each selectively of differing materials, hardness, form, performance characteristics and size.

15. Tooth cleaning instrument according to claim 1, wherein the vibration amplitudes of the tooth cleaning tool are directed selectively longitudinally and transversely of the longitudinal central axis of the handpiece.

* * * * *